United States Patent [19]

Jost et al.

[11] Patent Number: 4,596,680

[45] Date of Patent: Jun. 24, 1986

[54] PROCESS FOR MANUFACTURING ARYL ETHERS HAVING DIFFERENT SUBSTITUENTS ON THE TWO AROMATIC RINGS

[75] Inventors: Philippe Jost, Vernaison; Pierre Le Perchec, Lyon; Bernard Sillion, Rocquencourt, all of France

[73] Assignees: Institut Francais du Petrole, Rueil-Malmaison; Centre National de la Recherche Scientifique (CNRS), Paris, both of France

[21] Appl. No.: 483,316

[22] Filed: Apr. 8, 1983

[30] Foreign Application Priority Data

Apr. 9, 1982 [FR] France .................. 82 06379

[51] Int. Cl.$^4$ .................. C07C 120/00; C07C 76/02; C07C 79/35
[52] U.S. Cl. .................. 560/424; 568/33; 568/585; 568/635; 564/171; 564/420; 560/73; 558/413; 558/416; 558/415
[58] Field of Search .................. 568/585, 635, 33; 260/465 F; 560/73; 564/171, 420

[56] References Cited

FOREIGN PATENT DOCUMENTS 1290148 3/1969 Fed. Rep. of Germany ...... 568/585

OTHER PUBLICATIONS

Morrison and Boyd, 3rd ed., (1973), 337–338.

*Primary Examiner*—Bernard Helfin
*Attorney, Agent, or Firm*—Millen & White

[57] ABSTRACT

A asymmetrical aryl ether of the formula

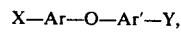

wherein Ar and Ar' are each a divalent aromatic radical, X and Y are electron attracting atoms or groups which differ from each other or have different positions on the corresponding aromatic radicals, is produced by heating together, in the presence of a basic catalyst, equimolecular amounts of two aryl carbonates of the formulas:

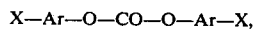

and

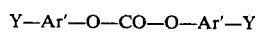

12 Claims, No Drawings

PROCESS FOR MANUFACTURING ARYL ETHERS HAVING DIFFERENT SUBSTITUENTS ON THE TWO AROMATIC RINGS

BACKGROUND OF THE INVENTION

This invention concerns the manufacture of aryl esters having different substituents on the two aromatic rings.

The diphenylether derivatives, when substituted with functional groups, are industrial products of particular interest in the plastics industry; particularly, they take part in the manufacture of thermostable materials. Other functionalized compounds are intermediates for insecticides of very high efficiency.

Processes leading to the formation of an ether linkage between two aromatic rings are continuously researched with a view to improving their yield and/or selectivity.

It is known from Ullman's work that an alkali phenate reacts with a halogenated aromatic derivative to form an ether linkage. When the aromatic rings are unsubstituted or substituted with nonelectron attracting groups, the reaction requires severe conditions. When the reaction is effected with halogenated derivatives and aromatic phenates carrying electron attracting groups, the reaction is highly exothermic and difficult to control, especially when operating with large amounts of materials. In all cases these reactions require the use of two different compounds, the phenate and the halogenated derivative.

German Pat. No. 1 290 148 and No. 2 104 201 describe a new reaction for the production of diphenylethers substituted with electron attracting groups; the results of these works have been again published by H. Witt, G. Holtschmidt and E. Muller (Angew. Chem. Internat. Edit. 9, 1970 (1) p. 67). The process is based on the thermal decomposition with base catalysis of the corresponding phenyl carbonates. This process has the advantage of making use of a single starting product, the substituted phenol, and of making it possible to follow the course of the extent of reaction, which occurs in bulk, by the carbon dioxide evolution.

This process is particularly adapted to the synthesis of diphenylethers substituted on each phenyl ring with identical electron attracting groups such as CN, $NO_2$, carboxylic ester or phenylsulfone, but it does not solve the problem of synthesizing diphenylether derivatives substituted with two different electron attracting groups and these products may constitute highly desirable raw materials for manufacturing plastic materials.

SUMMARY

The object of the invention is to provide a process for manufacturing aryl ethers of the general formula

 (I)

substituted on each aromatic ring with a different electron attracting substituent, by means of a reaction occurring with a high yield and a good selectivity (Ar, Ar', X and Y will be defined hereinafter). The process of the invention generally consists of heating together, as a molten mass or as a solution, substantially equimolecular amounts of two aryl carbonates, each of which is di-substituted in a symmetrical manner, and complying respectively with the general formulae:

 (II)

and

 (III)

in the presence of a basic catalyst.

Whereas the expected result should have been the formation of an equimolecular mixture of the two corresponding ethers

 (IV)

and

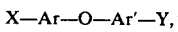 (V), as a result of a process of intramolecular $CO_2$ removal, or the formation of a mixture of the three ethers (I), (IV) and (V), in statistical proportions, it is observed in fact that the asymmetrical product (I) is formed with a high yield with respect to the starting carbonates.

This unexpected selectivity, resulting from a still unknown mechanism, is at the base of the invention. Thus the invention provides a process for manufacturing, with high yields, asymmetrical aryl ethers complying with the general formula

, wherein Ar and Ar' are each a divalent aromatic radical comprising one or more rings (derived for example from benzene, naphthalene or anthracene, preferably a phenylene radical), X and Y are each an atom or group of substantial electron attracting character when bonded to the aromatic radical and are different from each other by their nature and/or by their respective positions on the radicals Ar and Ar', at least one and preferably the two substituents X and Y being so placed on the radicals Ar and Ar' as to have an action on the bond with the oxygen atom, i.e. in 2 (ortho) or 4 (para) position, or still in peri position when the considered radical (Ar or Ar') contains at least two fused rings. In addition it is desirable that the involved electron attracting groups be not sensitive to the action of the bases.

The electron attracting substituents X and Y are more particularly selected from $-NO_2, -CN, -COO\ Ar''$, $-SO_2Ar''$ (wherein Ar'' is a monovalent aromatic radical) and $-CONR^1R^2$ groups ($R^1$ and $R^2$ being each a hydrogen atom or an alkyl group of 1 to 10 carbon atoms). Preferably one of the substituents, for example X, is a $-NO_2$ group, the other, Y, being optionally selected from the above-mentioned groups.

The process of the invention comprises heating, for example at a temperature from 190° to 280° C., substantially equimolecular amounts of the two aryl carbonates, each symmetrically substituted, and complying with the general formulas

 (II), and

 (III)

wherein Ar, Ar', X and Y are defined as above, in the presence of a basic catalyst, consisting in particular of a salt of an alkali metal, for example a carbonate, a phenate, an acetate or an alcoholate. In most cases potassium carbonate is used. The catalyst amount is from 0.1 to 5 moles per 100 moles of the starting carbonates.

The reaction may take place between the two aryl carbonates in a molten state (in bulk) or as a solution in an organic solvent such, for example, as nitrotoluene or acetonitrile.

The symmetrically substituted aryl carbonates may be obtained from the corresponding phenols by any known method.

Typical symmetrically substituted aryl carbonates which can be reacted with each other according to the process of the invention are:
bis(4-nitrophenyl)carbonate;
bis(3-nitrophenyl)carbonate;
bis(4-cyanophenyl)carbonate;
bis(2-phenoxy-carboxyphenyl)carbonate;
bis(4-phenylsulfonyl-phenyl)carbonate; and
bis(2-N,N-dimethylcarbamoylphenyl)carbonate.

Preferably one of the involved aryl carbonates, for example X—Ar—O—CO—Ar—X, is symmetrically substituted by two nitro groups in position 2 or in position 4. For example bis(4-nitrophenyl)carbonate is used. The second carbonate Y—Ar'—O—CO—O—Ar'—Y may then be specifically bis(3-nitrophenyl)carbonate, bis(4-cyanophenyl)carbonate, bis(2-phenoxy-carboxyphenyl)carbonate or bis(4-phenylsulfonyl-phenyl)carbonate, already mentioned above. The decarboxylation reaction, preferably catalyzed by potassium carbonate, gives high selectivities and high yields, for example at least about 75% with respect to the starting carbonates. The asymmetrical aryl ethers, obtained with good yields by the process of the invention, are industrial products particularly useful in the plastic materials industry, mainly for manufacturing certain thermostable materials.

In particular, the aryl ethers substituted with one or more nitro groups (—NO$_2$) may be subjected to a hydrogenation treatment, so as to convert the nitro group(s) to primary amine(s) groups.

Among the so obtained products, those having two primary amine groups or a primary amine group and a carboxylic group, are of interest in the manufacture of thermostable polymers by polycondensation with themselves (this is the case, for example, of the autocondensation of 2-(4'-aminophenoxy)phenyl benzoate) or with suitable antagonistic reactants having primary amine groups, hydroxy groups and/or monocarboxylic groups (acids or esters) or dicarboxylic groups (anhydrides, hemiesters and vicinal diesters). From these various reactants it is possible to prepare polycondensates containing esters or amides linkages or still heterocyclic linkages, particularly imides or quinazolones rings.

The following examples illustrate the invention without limiting the scope thereof. Examples 2, 5 and 7 are given by way of comparison.

EXAMPLE 1

Preparation of phenyl 2-(4'-nitrophenoxy)benzoate

A mixture of bis(2-phenoxy-carboxy phenyl)carbonate (9.1 g, i.e. 0.02 mole) and bis(4-nitrophenyl)carbonate (6.1 g, i.e. 0.02 mole) is heated to 240° C. in the presence of 0.1 g (0.0007 mole) of K$_2$CO$_3$. The reaction is very fast and 960 cm$^3$ (0.04 mole) of CO$_2$ at 20° C., corresponding to the theoretical amount, are recovered in less than 15 mn. The mixture is allowed to cool 80 cm$^3$ of a toluene-ethanol mixture (50/50 V/V) are introduced and brought to reflux. After hot filtration and cooling, a product crystallizes. It is filtered and dried under vacuum. A product, which is phenyl 2-(4'-nitrophenoxy)benzoate is obtained in an amount of 10.3 g (yield 77% m.p. 139° C.). By evaporation the mother liquor and recrystallizing the oil in 40 cm$^3$ of ethanol, an additional amount of 1.6 g is obtained, so that the total yield of phenyl 2-(4'nitrophenoxy) benzoate reaches 89%.

EXAMPLE 2 (COMPARATIVE)

Preparation of methyl 2-(4'-nitrophenoxy)benzoate

A mixture of bis(2-methoxy-carboxy phenyl)carbonate (6.6 g, i.e. 0.02 mole) and bis(4-nitrophenyl)carbonate (6.1 g, i.e. 0.02 mole) is heated to 240° C. in the presence of 0.2 g of anhydrous potassium carbonate (0.0014 mole). The reaction is fast and, after 20 mn, the mixture is allowed to cool and 60 cm$^3$ of methanol, hot filtered, are introduced. Methanol is evaporated and a preparative column chromatography of the raw reaction product gives 36% (3.50 g) of methyl 2-(4'-nitrophenoxy)benzoate; m.p. 74° C. (lit: 76° C.). The yield is not so good with methyl ester groups, carried by one of the carbonates than with phenyl ester groups, everything else remaining unchanged.

EXAMPLE 3

Preparation of 3,4'di(nitrophenyl)ether

A mixture of bis(3-nitrophenyl)carbonate (6.1 g, i.e. 0.02 mole), bis(4-nitrophenyl)carbonate (6.1 g, i.e. 0.02 mole) and 0.2 g of potassium carbonate (0.0014 mole) is heated to 240° C. under stirring at ordinary pressure. 940 cm$^3$ of CO$_2$ (0.039 mole) are recovered in 45 mn. The mixture is taken up with 120 cm$^3$ of an ethanol/chloroform mixture (80/20 by volume). After recrystallization, filtering and drying, 7.9 g of 3,4'di(nitrophenyl)ether (75%) are recovered. This product as analyzed by highly performance liquid chromatography, is free of 4,4'di(nitrophenyl)ether. It melts at 122° C. (lit: 124° C.).

In this example the substituents were of the same nature on both carbonates but in different positions, meta position with respect to the oxygen atom bond on one of them and para position on the other.

EXAMPLE 4

Preparation of 4-(4'-nitrophenoxy)benzonitrile

A mixture of bis(4-cyanophenyl)carbonate (2.6 g, i.e. 0.01 mole) with bis(4-nitrophenyl)carbonate (3.0 g, i.e. 0.01 mole) and potassium carbonate (0.1 g, i.e. 0.0007 mole), is heated to 230° C. for 1 hour. The mixture is dissolved into 25 cm$^3$ of toluene, hot-filtered and crystallized. A first amount of 3.3 g of 4-(4'-nitrophenoxy)-benzonitrile is obtained (yield: 69%). By concentrating the remaining solution, a further amount of 0.6 g is obtained so that the total yield reaches 82%. The product melts at 150° C.

EXAMPLE 5 (COMPARATIVE)

Preparation of 4-(4'-nitrophenoxy)chlorobenzene

A mixture of bis(4-chlorophenyl)carbonate (5.7 g, i.e. 0.02 mole) with bis(4-nitrophenyl)carbonate (6.1 g, i.e. 0.02 mole) and K$_2$CO$_3$ (0.2 g, i.e. 0.0014 mole) is heated to 240° C. for 4 hours. 400 cm$^3$ of CO$_2$ (i.e. about 0.017 mole) are recovered. At the end and after cooling 10 cm$^3$ of a concentrated ammonia solution and 40 cm$^3$ of dichloromethane are introduced. After 10 mn, 20 cm$^3$ of a cold 5% sodium hydroxide are added. The organic phase is settled, dried and evaporated. By column liquid chromatography the dinitro-diphenyl ether is separated from the 4(4'-nitrophenoxy)chlorobenzene (m.p.: 76° C., 1.0 g, i.e. a 10% yield). The chlorine substituent (not electron attracting) does not provide good yields.

EXAMPLE 6

Preparation of 4(4'-nitrophenoxy)diphenylsulfone

A mixture of bis(4-phenylsulfonyl phenyl)carbonate (4.9 g, i.e. 0.01 mole) with bis(4-nitrophenyl)carbonate (3.0 g, i.e. 0.01 mole) and potassium carbonate (0.1 g, i.e. 0.0007 mole) is heated to 240° C. After one hour, 20 cm³ of ethyl acetate are added at reflux. The whole is hot-filtered. A solid crystallizes and is separated. 6.4 g of 4-(4'-nitrophenoxy)diphenylsulfone, melting at 126°–127° C., are obtained (yield: 90%).

EXAMPLE 7 (COMPARATIVE)

Preparation of methyl 4-(4'-nitrophenoxy)orthophthalate

A mixture of bis(3,4-di-methoxycarbonylphenyl)carbonate (6.9 g, i.e. 0.0155 mole) with bis(4-nitrophenyl)carbonate (4.7 g, i.e. 0.0155 mole) and potassium carbonate (0.1 g, i.e. 0.0007 mole) is heated to 240° C. for a period of 20 mm, at the end of which the expected $CO_2$ theoretical amount is reached (750 cm³, i.e. 0.032 mole). The raw reaction product is dissolved into 50 cm³ of dichloromethane and a preparative chromatography over silica provides 1.7 g of nitroanisole (0.011 mole), 0.8 g of bis(4-nitrophenyl)ether (0.003 mole) and 2.9 g of a substantially 50/50 mixture of methyl 4-(4'-nitrophenoxy)orthophthalate with methyl 4,4'oxy di-orthophthalate. The yield of dissymmetrical ether is only 14%.

EXAMPLE 8

Preparation of N N-dimethyl, 2-(4'-nitrophenoxy)benzamide

A mixture of bis(2-NN-dimethyl-carbamoyl phenyl)carbonate (7.12 g, i.e. 0.02 mole) with bis(4-nitrophenyl)carbonate (6.1 g, i.e. 0.02 mole) and $K_2CO_3$ (0.1 g, i.e. 0.0007 mole), is heated to 230° C. After 20 minutes the mixture is cooled and taken up with ethyl acetate. Chromatography in a silica column provides 6.3 g (yield of 55%) of NN-dimethyl, 2-(4'-nitrophenyl)benzamide, consisting of a very viscous non-crystallizable oil.

EXAMPLE 9

Preparation of phenyl 2-(4'-nitrophenoxy)benzoate

The operating conditions are those described in example 1, except that 0.2 g of potassium acetate (i.e. 0.002 mole) is used instead of the potassium carbonate.

The reaction, conducted at 240° C., is complete after 20 minutes. The product, recovered as in example 1, gives 9.5 g of phenyl 2-(4'-nitrophenoxy)benzoate (yield: 71%).

The following Table summarizes the results of the preceding examples:

| EXAMPLE No. | X | Y | XY ETHER YIELD |
|---|---|---|---|
| 1 | 4-$NO_2$ | 2-C(=O)Oφ | 89% (a) |
| 2 (comp.) | 4-$NO_2$ | 2-C(=O)$OCH_3$ | 36% (b) |
| 3 | 4-$NO_2$ | 3-$NO_2$ | 75% (a) |
| 4 | 4-$NO_2$ | 4-CN | 82% (a) |
| 5 (comp.) | 4-$NO_2$ | 4-Cl | 10% (b) |
| 6 | 4-$NO_2$ | 4-$SO_2$—φ | 90% (a) |
| 7 (comp.) | 4-$NO_2$ | 3,4 di-C(=O)$OCH_3$ | 14% (b) |
| 8 | 4-$NO_2$ | 2-$CON(CH_3)_2$ | 55% (b) |
| 9 | 4-$NO_2$ | 2-C(=O)Oφ | 71% (a) |

(a) yield to recrystallized product.
(b) yield to the product isolated by chromatography in a silica column.

This Table shows the importance of the presence of electron attracting groups on both rings (compare Examples 1, 3, 4, 6 to Example 5 where one of the two rings is substituted with a chlorine atom). The Table also makes apparent the importance of the selection of the electron attracting groups, which must not be sensitive to the action of bases (compare Example 1, where one of the rings is substituted by a phenyl ester, to Example 2, where the substituent is a methyl ester and to Example 7, where the substituent consist of 2 methyl ester groups).

EXAMPLE 10

Hydrogenation of phenyl 2-(4-nitrophenyl)benzoate 9 g of phenyl 2-(4'-nitrophenoxy)benzoate, prepared as described in Example 1, are contacted with hydrogen in 50 cm³ of ethanol, in the presence of 5% palladium (100 mg) on coal. After recrystallization in 100 cm³ of a methanol-water mixture (50—50 by volume), 7.52 g of phenyl 2-(4'-aminophenoxy)benzoate (m.p. 102° C.) are obtained (yield: 92%).

What is claimed is:

1. A process for the manufacture of an asymmetrical aryl ether of the general formula:

$$X-Ar-O-Ar'-Y$$

wherein Ar and Ar' are each a divalent aromatic radical having one or more rings, X and Y, as incorporated in said ether, are each an atom or group having electron-attracting properties, insensitive to the action of bases, and differing from each other by their nature and/or by their respective positions in radicals Ar or Ar', at least one of the X and Y substituents being, on the Ar or Ar' radical, in ortho, pera or peri position with respect to the oxygen atom bond and wherein neither X nor Y is chlorine, said process being characterized by heating sufficiently together, in the presence of a basic catalyst, substantially equal amounts of two aryl carbonates complying with the general formulas:

X—Ar—O—CO—O—Ar—X, and

Y—Ar'—O—CO—O—Ar'—Y wherein Ar, Ar', X and Y are defined as above to obtain a higher than statistical proportion of said assymetrical ether and separating the formed asymmetrical aryl ether.

2. A process according to claim 1, wherein the Ar and Ar' radicals are phenylene radicals and at least one of the X and Y substituents on the Ar or Ar' radical is in ortho or para position with respect to the oxygen atom bond.

3. A process according to claim 1, characterized by the selection of X and Y from the groups consisting of —$NO_2$, —CN, —COOAr", —$SO_2$Ar", wherein Ar" is a monovalent aromatic radical, and —CON$R^1R^2$, wherein $R^1$ and $R^2$ are each a hydrogen atom or an alkyl group having 1 to 10 carbon atoms.

4. A process according to claim 1, characterized in that X is a —$NO_2$ group and Y is selected from the groups consisting of —$NO_2$, —CN, —COOAr", —$SO_2$Ar", wherein Ar" is a monovalent aromatic radical, and —CON$R^1R^2$ wherein $R^1$ and $R^2$ are each a hydrogen atom or an alkyl group having from 1 to 10 carbon atoms.

5. A process according to claim 1, characterized in that the two starting carbonates are heated, in molten state, at a temperature from 190° to 280° C.

6. A process according to claim 1, characterized in that the two starting carbonates are heated, as solution, at a temperature from 190° to 280° C.

7. A process according to claims 1 to 6, characterized in that the basic catalyst is selected from the alkali metal carbonates, phenates, acetates and alcoholates.

8. A process according to one of claim 1, characterized in that the catalyst is used in an amount of 0.1 to 5 moles per 100 moles of the starting carbonate.

9. A process according to claim 1, wherein the aryl ether is obtained with a yield of at least 75%.

10. A process according to claim 1, characterized in that the two aryl carbonates are different and selected from:
bis-(4-nitrophenyl)carbonate,
bis-(3-nitrophenyl)carbonate,
bis-(4-cyanophenyl)carbonate,
bis-(2-phenoxy-carboxyphenyl)carbonate,
bis-(4-phenylsulfonylphenyl)carbonate, and
bis-(2-N,N-dimethylcarbamoyl-phenyl)carbonate.

11. A process according to claim 10, characterized in that one of the two aryl carbonates is bis-(4-nitrophenyl)carbonate, and the other is selected from:
bis-(3-nitrophenyl)carbonate,
bis-(4-cyanophenyl)carbonate,
bis-(2-phenoxy-carboxyphenyl)carbonate, and
bis-(4-phenylsulfonylphenyl)carbonate
and in that the basic catalyst is potassium carbonate.

12. A process according to claim 1, characterized by the preparation of a dissymmetrical aryl ether of the formula X—Ar—O—Ar'—Y wherein at least one of the X and Y substituents is a —$NO_2$ group and the subsequent hydrogenation of said aryl ether, converting the —$NO_2$ groups to primary amine groups.

* * * * *

UNITED STATES PATENT AND TRADEMARK OFFICE
CERTIFICATE OF CORRECTION

PATENT NO. : 4,596,680
DATED : June 24, 1986
INVENTOR(S) : PHILIPPE JOST ET AL

It is certified that error appears in the above-identified patent and that said Letters Patent is hereby corrected as shown below:

Column 8, line 4: reads "7. A process according to claims 1-6, characterized"
should read -- 7. A process according to claim 1, characterized --

Column 8, line 7: reads "8. A process according to one of claim 1, character-"
should read -- 8. A process according to claim 1, character- --

Column 8, line 9: reads "moles per 100 moles of the starting carbonate."
should read -- moles per 100 moles of the starting carbonates. --

Column 8, line 30: reads "the preparation of a dissymmetrical aryl ether of the"
should read -- the preparation of an assymetrical aryl ether of the --

Signed and Sealed this

Sixteenth Day of September 1986

[SEAL]

Attest:

DONALD J. QUIGG

Attesting Officer

Commissioner of Patents and Trademarks